US006659197B2

(12) United States Patent
Cooper

(10) Patent No.: US 6,659,197 B2
(45) Date of Patent: Dec. 9, 2003

(54) METHOD FOR DETERMINING DRILLING FLUID PROPERTIES DOWNHOLE DURING WELLBORE DRILLING

(75) Inventor: Iain Cooper, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 175 days.

(21) Appl. No.: 09/923,750

(22) Filed: Aug. 7, 2001

(65) Prior Publication Data

US 2003/0029640 A1 Feb. 13, 2003

(51) Int. Cl.[7] .......................... E21B 21/08; E21B 47/06
(52) U.S. Cl. ...................... 175/48; 175/50; 166/250.01; 73/152.22; 73/152.52
(58) Field of Search .................. 166/250.01, 250.07; 175/48, 50; 73/152.22, 152.31, 152.52

(56) References Cited

U.S. PATENT DOCUMENTS

| | | | | |
|---|---|---|---|---|
| 2,348,192 A | * | 5/1944 | Chambers | 73/152.37 |
| 3,468,158 A | * | 9/1969 | Chien | 73/54.05 |
| 3,885,429 A | * | 5/1975 | Megyeri et al. | 73/152.22 |
| 3,952,577 A | * | 4/1976 | Hayes et al. | 73/54.04 |
| 4,274,283 A | * | 6/1981 | Maus et al. | 73/152.22 |
| 4,535,851 A | * | 8/1985 | Kirkpatrick et al. | 175/38 |
| 4,641,535 A | * | 2/1987 | Malguarnera | 73/861.01 |
| 4,821,564 A | | 4/1989 | Pearson et al. | |
| 4,941,951 A | * | 7/1990 | Sheppard et al. | 175/48 |
| 5,042,296 A | * | 8/1991 | Burgess | 73/152.19 |
| 5,513,528 A | | 5/1996 | Holenka et al. | |
| 5,850,621 A | * | 12/1998 | Cartalos et al. | 702/9 |
| 6,029,755 A | * | 2/2000 | Patel | 175/50 |
| 6,057,784 A | | 5/2000 | Schaaf et al. | |
| 6,058,771 A | * | 5/2000 | Johnson et al. | 73/152.21 |
| 6,148,912 A | * | 11/2000 | Ward | 166/250.07 |
| 6,176,323 B1 | * | 1/2001 | Weirich et al. | 175/40 |
| 6,189,612 B1 | * | 2/2001 | Ward | 166/250.07 |
| 6,220,087 B1 | | 4/2001 | Hache et al. | |
| 6,296,056 B1 | * | 10/2001 | Ward | 166/250.07 |
| 6,412,337 B1 | * | 7/2002 | Arzate et al. | 73/54.09 |

FOREIGN PATENT DOCUMENTS

WO WO 01/02832 1/2001

OTHER PUBLICATIONS

Maglione et al., "In–Situ Rheological Characterization of Drilling Mud," *SPE Journal*, vol. 5, No. 4, pp. 377–386 (Dec. 2000).

Alun Whittaker ed., *Theory and Application of Drilling Fluid Hydraulics*, Exlog Series of Petroleum Geology, IHRDC Publishers, Boston MA, pp. 21–22 (1985).

Wm Press et al., *Numerical Recipes in C*, 2nd Ed., Cambridge University Press, pp. 379–381 (1988, 1992).

Haciislamoglu et al., "Practical Pressure Loss Predictions in Realistic Annular Geometries," *SPE 28304* (1994).

T. Reed et al., "A New Model for Laminar, Transitional, and Turbulent Flow of Drilling Muds," *SPE 25456* (1993).

* cited by examiner

*Primary Examiner*—William Neuder
*Assistant Examiner*—T Shane Bomar
(74) *Attorney, Agent, or Firm*—Kevin P. McEnaney; Brigitte L. Jeffery; John J. Ryberg

(57) ABSTRACT

Determining the downhole rheological properties of a wellbore fluid. The method includes moving the wellbore fluid through a wellbore tool assembly into a wellbore at a first flow rate. A pressure is measured at a first position proximate a bottom of the wellbore. A pressure is measured at a second position in the wellbore axially separated from the first position. The wellbore fluid is then moved through the wellbore tool assembly at a second flow rate. Measuring pressure at the first and second positions is repeated, and at least one rheological property is determined from the pressure measurements.

22 Claims, 3 Drawing Sheets

METHOD FOR DETERMINING DRILLING FLUID PROPERTIES DOWNHOLE DURING WELLBORE DRILLING

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The invention relates generally to the field of measurements made during the drilling of wellbores. More specifically, the invention relates to methods for determining rheological properties of well fluid or drilling mud as they exist down in a wellbore during the actual drilling of the wellbore.

2. Background Art

Drilling wellbores for purposes such as petroleum production is generally performed using rotary drilling techniques. A rotary drill bit is coupled to one end of a drilling tool assembly, and the assembly is rotated while applying axial force to the bit. Drilling fluid, called "drilling mud" is pumped through the interior of the drilling tool assembly, and outward through appropriately selected orifices, called nozzles or jets, disposed in the body of the drill bit. The drilling mud that is discharged through the jets performs a number of functions, including cooling and lubricating the drill bit, applying hydrostatic pressure to the earth formations that have been drilled in order to control pressure of fluids in the pore spaces of the formations, and lifting drill cuttings generated by the bit to the earth's surface through an annular space between the drilled wellbore and the exterior of the drilling tool assembly.

To perform all these functions adequately, the hydraulic properties of the drilling mud, known in the art as "rheology" or "rheological properties", must be carefully controlled. Generally speaking, the rheological properties of the drilling mud are selected to meet a variety of performance criteria. These performance criteria include, for example that a circulating pressure loss in the annular space is not excessive, so that the drilling mud has an adequate capacity to lift the drill cuttings out of the wellbore, that excessive "swab" and "surge" pressures (reduced and excess hydrostatic pressures, respectively, deep in the wellbore, caused by movement of the drilling tool assembly out of and into the wellbore acting as a syringe) are avoided, and that erosion of susceptible clay-bearing earth formations is minimized, among other factors.

Drilling mud compositions commonly used in wellbore drilling have pseudo-plastic behavior under applied stresses. Various mathematical models have been developed to describe this behavior. One such model is known as the "Power law" model. Another model is known as the "Bingham Plastic" model. A fluid modeled using the Bingham Plastic model is presumed not to flow until an applied shear stress, $\tau$, exceeds a minimum value $\tau_0$. This minimum value of shear stress is known as the "yield point" (YP) of the particular drilling mud. At stress levels above the YP, changes in shear stress become proportional to the changes in the shear rate. The proportionality constant is known as the plastic viscosity (PV), represented in the equation below as $\gamma$. The Bingham Plastic model can be represented by the following expression:

$$\tau = \tau_0 + \mu_0 \gamma; \tau \geq \tau_0$$

There are various instruments known in the art for determining PV and YP for a particular drilling mud. Typically, these instruments are used at the earth's surface wherein a sample of the drilling mud is placed in the instrument and the properties of the drilling mud are determined. One such instrument is called a rotational, or Fann, viscosimeter. Typically, the Theological properties of mud are determined at surface temperature and pressure. The rheological properties which exist at the bottom of a wellbore as the wellbore is being drilled may be substantially different than those determined at the earth's surface. Various factors, including temperature, flow rate, hydrostatic pressure, presence of drill cuttings and dilution by fluids in the formations moving into the wellbore may cause the Theological properties downhole to be different than those measured at the earth's surface. More advanced rheometers are available for measuring the Theological parameters at elevated temperatures and pressures, however, they can only approximate the conditions at depth in a wellbore ("downhole") and do not yet extend to the high pressure regimes encountered in many wells.

On method known in the art for estimating rheological properties downhole is described, for example, in, *In-Situ Characterization of Drilling Mud*, Maglione et al., SPE Journal, vol. 5, no. 4 (December 2000). The method described in this reference includes measuring standpipe pressure and calculating an estimate of average values of mud parameters over the entire mud circulation system. The method disclosed in this reference, however, does not disclose how to make any explicit determination of mud Theological properties at or near the bottom of the wellbore, and certainly does not disclose how to do so during the actual drilling of the wellbore.

What is needed is a method for determining downhole drilling mud rheological properties that can be carried out substantially in real time as a wellbore is being drilled.

SUMMARY OF THE INVENTION

One aspect of the invention is a method is for determining Theological properties of a wellbore fluid. The method includes moving the wellbore fluid through a wellbore tool assembly into a wellbore at a first flow rate. A pressure is measured at a first position proximate a bottom of the wellbore in an annular space between the interior wall of the wellbore and the exterior of the wellbore tool assembly. A pressure is measured at a second position in the annular space axially separated from the first position. The wellbore fluid is then moved through the wellbore tool assembly at a second flow rate. Measuring pressure at the first and second positions is repeated, and at least one Theological property is determined from the pressure measurements.

Other aspects and advantages of the invention will be apparent from the following description and the appended claims.

DETAILED DESCRIPTION

Figure 1:
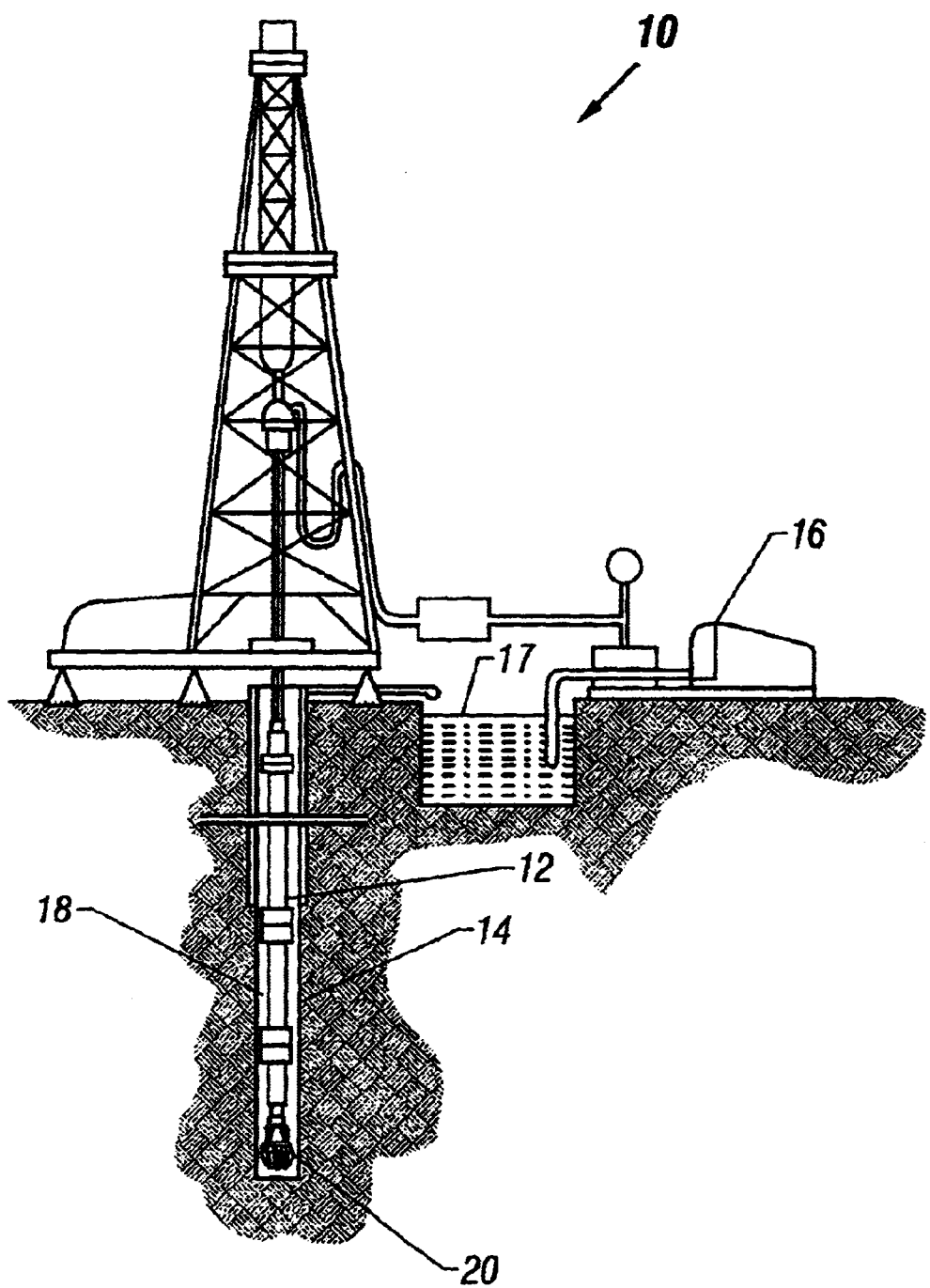
FIG. 1 shows an example of a wellbore being drilled through earth formations.

An example of a wellbore 14 being drilled through the earth is shown in FIG. 1. The wellbore 14 is drilled by a drilling rig 10 which raises and lowers a drilling tool assembly 12 out of and into the wellbore, while turning the drilling tool assembly 12. A drill bit 20 is coupled to the lower end of the drilling tool assembly 12. Mud pumps 16 at the rig 10 lift drilling mud from a tank or storage pit 17 and pump it through the interior of the drilling tool assembly 12. The mud travels out from nozzles (not shown) in the bit 20, and returns to the surface in an annular space 18 between the outside of the drilling tool assembly 12 and the wall of the wellbore 14. As is known in the art, the mud pumps 16 can be operated to result in a selected flow rate through the drilling tool string, or to provide a selected pressure at the earth's surface in the "standpipe" (pump outlet) side of the drilling fluid circulation system.

Figure 2:
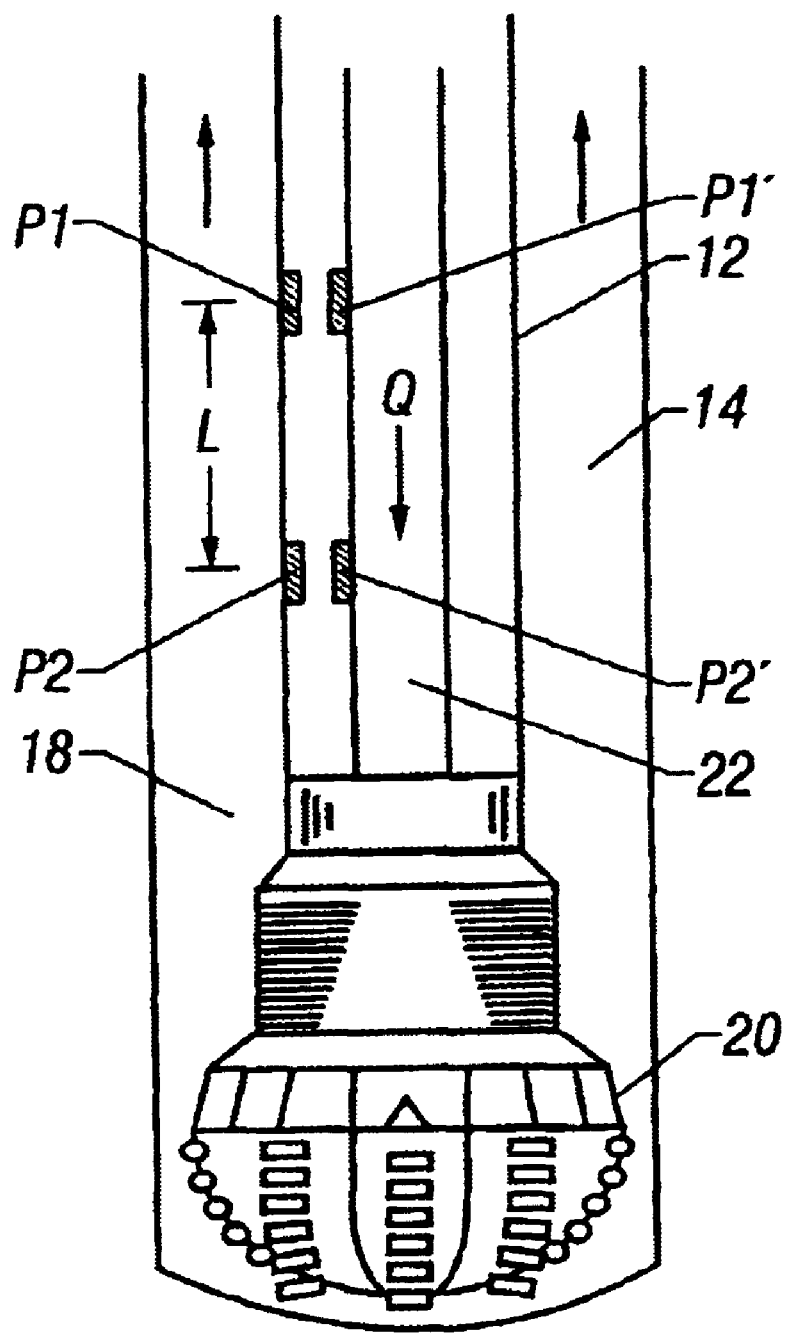
FIG. 2 shows a schematic example of pressure measurements being made near the bottom of the wellbore.

The principle of methods according to the invention can be better understood by referring to FIG. 2. Generally speaking, a pressure in the drilling fluid is measured at two spaced apart positions proximate the bottom of the wellbore 14, shown as P1 and P2 in FIG. 2. The pressure measurements may be made by any type of pressure sensor known in the art to be used for wellbore pressure measurement. Preferably, the pressure measurements are recorded and/or transmitted to the earth's surface by appropriate instrumentation (not shown) forming part of the drilling tool assembly 12. Preferably, the distance between the positions P1, P2 is such that there is a measurable difference in hydrostatic pressure between P1 and P2, as will be further explained.

The pressure measurements are assumed, for purposes of the description herein, both to be made from within the interior 22 of the drilling tool assembly 12, for example at positions P1' and P2'. However, the following analysis can be easily applied to pressure measurements both made within the annular space 18, for example at positions P1 and P2, or for one measurement made in the annular space 18 and one inside the drilling tool assembly 12, preferably just behind the bit 20. In the case where one pressure measurement is made inside the drilling tool assembly 12 and one is made outside in the annular space 18, it is necessary to adjust the pressure measurements for pressure drop across the bit nozzles (not shown). Methods for calculating pressure drop across the nozzles are well known in the art. The drilling tool assembly 12 may include any device known in the art which can make and record, and/or transmit to the earth's surface, measurements of various environmental parameters, formation properties, and/or drilling parameters. Such devices are well known in the art. See for example, U.S. Pat. No. 6,057,784 issued to Schaaf et al. Methods of transmission known in the art include modulating the flow of drilling mud through the drilling tool assembly 12, called "mud pulse telemetry."

The example configuration shown in FIG. 2 assumes that the drilling tool assembly 12 is substantially centered within the wellbore, and that the drilling tool assembly is oriented substantially vertically. In cases where the wellbore is deviated from vertical, an analysis may be performed which assumes that the drilling tool assembly 12 rests against the wall of the wellbore. Alternatively, an amount of offset between the wellbore wall and the drilling tool assembly (called "standoff"), where the drilling tool assembly 12 is neither centered nor against the wall of the wellbore ("eccentered") can be estimated from a caliper measurement, for example. Calipers for measuring an amount of standoff are known in the art. See for example, U.S. Pat. No. 5,513,528 issued to Holenka et al. Analysis of pressure difference between the two positions P1, P2 where the drilling tool assembly 12 is eccentered in the wellbore 14 will be further explained. It is further assumed, for simplicity of the analysis, that the drilling tool assembly 12 is not rotating when the pressure measurements are made.

First, determining rheological properties requires an estimate of static fluid pressure at each of the two positions P1, P2. One way to determine static fluid pressure is to measure the pressure at each position P1, P2 when the mud pumps (16 in FIG. 1) are turned off. Let the equivalent static pressure ("ESP"), effectively the hydrostatic pressure of the drilling mud column in the wellbore 14 at each of the two positions, P1 and P2, be represented by $ESP_1$ and $ESP_2$ respectively. For a typical logging while drilling ("LWD") instrument or drilling tool assembly, which includes mud pulse telemetry to transmit measurements to the earth's surface, measuring pressures while the mud pumps (16 in FIG. 1) are turned off to measure static pressure will require that the measurements be recorded in the drilling tool assembly 12. Measurement recording devices are known in the art. See for example, U.S. Pat. No. 5,513,528 issued to Holenka et al. Methods for determining the equivalent static pressure are also described in U.S. Pat. No. 6,220,087 issued to Hache et al.

The recorded pressure measurements can be sent to the earth's surface as soon as the mud pumps (16 in FIG. 1) are operated for the next part of a method according to the invention. Alternatively, the hydrostatic pressures may be estimated from the depths of the positions P1, P2 and the density of the drilling mud disposed in the wellbore 14.

Pressure measurements at each of the two positions, P1, P2 are then made at two different flow rates, in various embodiments of a method according to the invention. The flow rates should be selected such that there is statistically significant difference between the measurements made at each of the two positions P1, P2. The flow rates selected will depend, for example, on the distance between the two positions P1, P2, among other factors.

Pressure is measured at a first flow rate, $Q_1$ at each of the two sensors. The measurement of pressure at P1 and P2 is then repeated at a second flow rate $Q_2$. These pressures can be represented by $P_1(Q_1)$, $P_2(Q_2)$, respectively for each position P1, P2 at each flow rate. In embodiments of a method in which the calculations of rheological properties is to be performed during the drilling of the wellbore 14, it is necessary that the first and second flow rates be greater than the minimum flow rate needed to operate the telemetry system (not shown) in the drilling tool assembly 12.

A rheological model known in the art as the Heschel-Bulkley Theological model includes three rheological parameters. The Herschel-Bulkley model is described by the following parameters:

$$\tau = \tau_0 + \mu \dot{\gamma}^n; \tau \geq \tau_0$$

where $\tau_0$ represents the yield point, $\mu$ represents a "consistency index", and n represents a "flow behavior index." Details of the Herschel-Bulkley (and the Casson model, another two parameter model, also used in the drilling industry) are described in, *Theory and Application of Drilling Fluid Hydraulics*, Edited by Alun Whittaker, IHRDC Publishers, Boston (1985):

To determine all three parameters if the Herschel-Bulkely model is used requires that pressure measurements at each of the two positions P1, P2 be made at three different flow rates. As previously explained, if the determination of rheological properties is to be made during drilling using a logging-while-drilling instrument having mud telemetry, the flow rates should be more than the minimum flow rate needed to activate the mud telemetry system in the instrument.

Using the two measurements of pressure at each location P1, P2 made at each flow rate, for the Bingham Plastic (or other two-parameter models commonly used in the art) the following can be determined:

$$\Delta P_f(Q_1) = P_2(Q_1) - P_1(Q_1) - ESP_2 + ESP_1 \quad (2)$$

$$\Delta P_f(Q_2) = P_2(Q_2) - P_1(Q_2) - ESP_2 + ESP_1 \quad (3)$$

where $\Delta P_f$ represents the frictional pressure loss between the two positions P1, P2. The distance between the positions is represented by L.

In the following analysis the model used can be the previously referred to Bingham Plastic rheological model. The analysis can easily be extended to the Power Law, or other models such as Casson and Herschel-Bulkley fluid as defined above.

A critical Reynolds number for determining turbulent flow can be $Re_c = 2000$, and define as follows, based on the analysis for a Bingham Plastic fluid as described in, *Theory and Application of Drilling Fluid Hydraulics,* Edited by Alun Whittaker, IHRDC Publishers, Boston (1985):

$$\bar{v}_i = \frac{4Q_i}{\pi d^2},$$

for i=1,2, the two flow rates.

Then let for each i, $$\beta_i = 1 + \frac{6\mu_\infty \bar{v}_i}{\tau_0 d}$$

$$z_i = \left(\beta_i^2 + \sqrt{\beta_i^4 - 1}\right)^{1/3}$$

$$y_i = 2(z_i + 1/z_i)$$

$$x_i = \frac{1}{2}\left(\sqrt{y_i} - \sqrt{\frac{8\beta_i}{\sqrt{y_i}} - y_i}\right)$$

$$\Delta P_{f_i} = \frac{4L\tau_o}{x_i d} \quad (4)$$

where L represents the spacing between the sensors, To represents the YP, and $\mu_\infty$ represents the PV. The external diameter of the drilling tool assembly 12 is represented by d.

The effective Reynolds number, Re, for the flow can be calculated by the expression:

$$Re = \frac{\rho \bar{v}_i d}{\mu_\infty}$$

$$\mu_\infty = \frac{\Delta P_{f_i} d^2}{32 L \bar{v}_i}$$

If $Re \leq Re_c$ the pressure drop between P1 and P2 cab be determined by Eq.(4), otherwise:

$$f = 0.079 \, Re^{0.25}$$

$$\Delta P_{f_i} = \frac{2 f L \rho \bar{v}_i^2}{d} \quad (5)$$

The drilling mud density proximate the two positions P1, P2 can either be determined from surface measurements of mud density, can be inferred from the static mud pressure and knowledge of the depth of the pressure sensor, or inferred from other measurements, such as that obtained from a gamma-ray density well logging instrument, or other density-neutron devices.

The frictional pressure drop can be modified by a factor that accounts for eccentering of the drilling tool assembly 12 in the wellbore 14. The modification factor will be explained later herein.

The expressions above represent two non-linear equations for determining $\tau_0$ and $\mu_\infty$ (at the two different flow rates). These equations can now be solved to determine the PV and YP at the bottom of the wellbore 14 proximate to the positions P1 and P2. A multi-dimensional minimization technique or a multi-dimensional Newton-Raphson method could be used as solution techniques. See, for example, B. Flannery et al., Numerical Recipes, Cambridge University Press (1989). If the Herschel-Bulkley Theological model is used, three different flow rates must be used as previously explained. The solution scheme to determine the Herschel-Bulkley parameters from the measured pressures can be taken from the analysis disclosed in the Maglione et al. reference cited earlier herein.

The following constraints may be placed on initial guesses of PV and YP to improve the chance of a numerical root finder obtaining the solution promptly. First, both the PV and YP must be positive numbers. Additionally, a first guess of the PV and YP at downhole conditions (conditions proximate the positions P1 and P2) can be based on the values obtained by measurement under conditions at the earth's surface or in the laboratory.

Frictional pressure loss calculations in narrow annuli of "slim-hole" operations, and sometimes coiled tubing operations, require accurate pressure loss predictions. Haciislamoglu and Cartalos[i] have developed easy-to-use, realistic correlations for laminar, transitional, and turbulent flow regimes that have been validated by experimental data for Power Law model fluids. See Haciislamoglu et al., *Practical Pressure Loss Predictions in Realistic Annular Geometries,* paper no. 28034, Society of Petroleum Engineers, Richardson, Tex. (1994). A "Power Law model index" n, can be related to Bingham Plastic model parameters by standard relationships between the two models:

$$\tau_0 \theta_{600} - 2(\theta_{600} - \theta_{300}) \quad (6)$$

$$\mu_\infty \theta_{600} - \theta_{300} \quad (7)$$

where the yield stress is expressed in units of $lbf/100 \, ft^2$ and the plastic viscosity is expressed in centipoise. The Power Law flow behavior index n is calculated by the expression:

$$n = 3.32 \log\left(\frac{\theta_{600}}{\theta_{300}}\right) \quad (8)$$

where $\theta_{600}$ represents Fann viscosity at 600 RPM and $\theta_{300}$ represents Fann viscosity at 300 RPM. Therefore:

$$n = 3.32 \log\left(\frac{2\mu_\infty + \tau_0}{\mu_\infty + \tau_0}\right) \quad (9)$$

Figure 3:
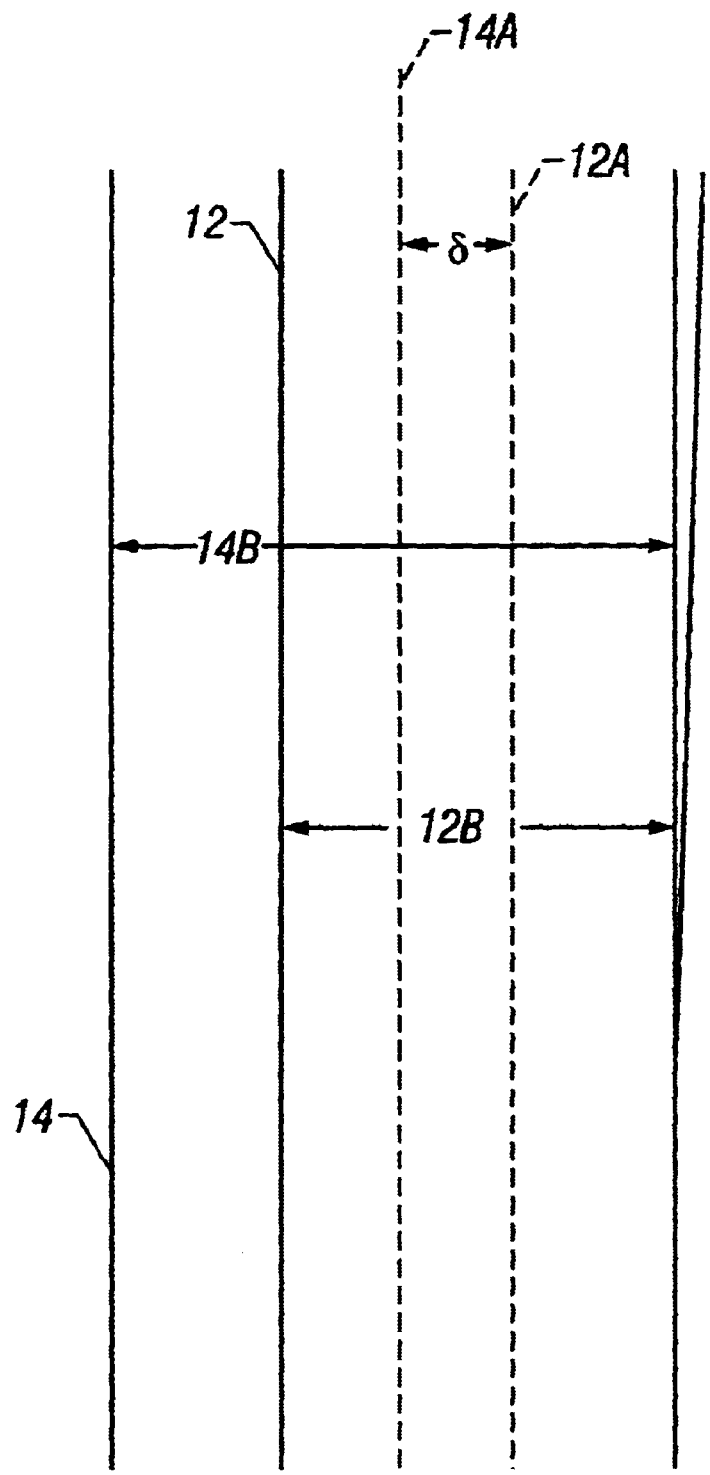
FIG. 3 shows a schematic example of a drilling tool assembly centered in a wellbore.

A non-dimensional degree of eccentering (offset) can be defined as follows:

$$e = \frac{\delta}{r_o - r_i} \quad (10)$$

where $\delta$ represents the offset, shown in FIG. 3 as a separation between a centerline of the drilling tool assembly 12A and a centerline of the wellbore 14A, and $r_o$, $r_1$ represent, respectively, outer and inner radii of the annular geometry, shown as diameters (2× radius) 14B and 12B in FIG. 3.

A ratio of the pressure drop (R), which as previously explained, may be used to correct the pressure measurements when the drilling tool assembly 12 is not centered in the wellbore 14. As explained in T. Reed et al., *A New Model for Laminar, Transitional and Turbulent Flow of Drilling Muds*, paper no. 25456, Society of Petroleum Engineers, Richardson, Tex. (1993), the following expressions apply to a uniformly eccentric annulus in laminar flow:

$$R_{lam} = \quad (11)$$
$$1 - 0.072 \frac{e}{n}\left(\frac{D_i}{D_o}\right)^{0.8454} - 1.5 e^2 \sqrt{n}\left(\frac{D_i}{D_o}\right)^{01852} + 0.96 e^3 \sqrt{n}\left(\frac{D_i}{D_o}\right)^{0.2527}$$

For turbulent flow, a slightly different relation is obtained as follows:

$$R_{turb} = 1 - 0.048\frac{e}{n}\left(\frac{D_i}{D_o}\right)^{0.8454} - \quad (12)$$
$$(2/3) e^2 \sqrt{n}\left(\frac{D_i}{D_o}\right)^{01852} + 0.285 e^3 \sqrt{n}\left(\frac{D_i}{D_o}\right)^{0.2527}$$

In the transitional flow regime between laminar and turbulent flow, R varies with the Reynolds number in a complex manner. The Reed et al reference cited above provides tables from which an approximate value for the eccentricity effect is obtained. However, given that in eccentric flow the instantaneous eccentric position of the drilling tool assembly 12 affects the time/Reynolds number at which the transition to turbulent flow occurs, a steady-state approximation can be made to represent this complex scenario.

What is claimed is:

1. A method for determining rheological properties of a wellbore fluid, comprising:
   estimating a static pressure at a first position proximate a bottom of the wellbore, and
   a static pressure at a second position axially separated from the first position;
   moving the wellbore fluid through a wellbore tool assembly into a wellbore at a first flow rate;
   measuring a pressure at the first and the second positions;
   moving the wellbore fluid through the wellbore tool assembly at a second flow rate;
   repeating measuring a pressure at the first and second positions; and
   determining at least one rheological property from the pressure measurements.

2. The method as defined in claim 1 wherein the estimating the static pressure comprises measuring pressure at the first and the second locations wherein the wellbore fluid is substantially static.

3. The method as defined in claim 1 wherein the estimating the static pressure comprises estimating a pressure at each of the first and the second positions from a density of the wellbore fluid determined at the earth's surface.

4. The method as defined in claim 1 wherein the first position and the second positions are located in an annular space between a wall of the wellbore and an exterior surface of the wellbore tool assembly.

5. The method as defined in claim 1 wherein the first position and the second position are located in an interior of the wellbore tool assembly.

6. The method as defined in claim 1 further comprising measuring pressure at the first and the second positions while moving the wellbore fluid at a third flow rate, and determining three rheological parameters from the pressure measurements.

7. The method as defined in claim 1 wherein the well tool assembly is substantially concentric with the wellbore.

8. The method as defined in claim 1 further comprising adjusting the pressure measurements for the well tool assembly being eccentered in the wellbore.

9. The method as defined in claim 1 wherein the at least one rheological property comprises plastic viscosity.

10. The method as defined in claim 1 wherein the at least one rheological property comprises yield point.

11. The method as defined in claim 1 wherein the at least one rheological property comprises Power Law model fluid behavior index.

12. The method as defined in claim 1 wherein a difference in the pressure measurements between the first position and the second position is correlated to a Bingham Plastic model fluid.

13. A method for determining rheological properties of a wellbore fluid, comprising:
   measuring a static fluid pressure at a first position proximate the bottom of the wellbore and a static fluid pressure at a second position proximate the bottom of the wellbore and axially spaced apart from the first position, the measuring;
   recording the static pressure measurements in a tool assembly disposed in the wellbore
   moving the wellbore fluid through a wellbore tool assembly into a wellbore at a first flow rate;
   measuring fluid pressure at the first position and at the second position at the first flow rate;
   moving the wellbore fluid through the wellbore tool assembly at a second flow rate;
   repeating measuring pressure at the first and second positions at the second flow rate;
   transmitting the recorded pressure measurements and the pressure measurements made at the first and second flow rates to the earth's surface; and
   determining at the earth's surface at least one rheological property from the pressure measurements.

14. The method as defined in claim 13 wherein the first position and the second position are located in an annular space between a wall of the wellbore and an exterior surface of the wellbore tool assembly.

15. The method as defined in claim 13 wherein the first position and the second position are located in an interior of the wellbore tool assembly.

16. The method as defined in claim 13, further comprising measuring pressure at the first and the second positions while moving the wellbore fluid at a third flow rate, and determining three rheological parameters from the pressure measurements at the first, second and third flow rates.

17. The method as defined in claim 13 wherein the well tool assembly is substantially concentric with the wellbore.

18. The method as defined in claim 13 further comprising adjusting the pressure measurements for the well tool assembly being eccentered in the wellbore.

19. The method as defined in claim 13, wherein the at least one rheological property comprises plastic viscosity.

20. The method as defined in claim 13 wherein the at least one rheological property comprises yield point.

21. The method as defined in claim 13 wherein the at least one rheological property comprises Power Law model fluid behavior index.

22. The method as defined in claim 13 wherein a difference in the pressure measurements between the first position and the second position is correlated to a Bingham Plastic model fluid.

* * * * *